(12) United States Patent
Sasaki et al.

(10) Patent No.: US 9,821,330 B2
(45) Date of Patent: Nov. 21, 2017

(54) ELECTROSTATIC ATOMIZER

(71) Applicant: SUMITOMO CHEMICAL COMPANY, LIMITED, Tokyo (JP)

(72) Inventors: Takashi Sasaki, Tokyo (JP); Van Thanh Dau, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 91 days.

(21) Appl. No.: 14/649,766

(22) PCT Filed: Dec. 5, 2013

(86) PCT No.: PCT/JP2013/082654
§ 371 (c)(1),
(2) Date: Jun. 4, 2015

(87) PCT Pub. No.: WO2014/088050
PCT Pub. Date: Jun. 12, 2014

(65) Prior Publication Data
US 2016/0184843 A1   Jun. 30, 2016

(30) Foreign Application Priority Data

Dec. 7, 2012   (JP) .................................. 2012-268777

(51) Int. Cl.
*A61M 15/02* (2006.01)
*A61M 11/00* (2006.01)
(Continued)

(52) U.S. Cl.
CPC ............... *B05B 5/03* (2013.01); *A61M 11/00* (2013.01); *A61M 15/02* (2013.01); *B05B 5/0255* (2013.01);
(Continued)

(58) Field of Classification Search
CPC ........ B05B 5/03; B05B 5/0255; A61M 11/00; A61M 15/02
(Continued)

(56) References Cited

U.S. PATENT DOCUMENTS 2,453,080 A * 11/1948 Shimp .................... G01F 11/32
141/375
3,092,106 A *  6/1963 Butler ................... A61M 5/162
222/159

(Continued)

FOREIGN PATENT DOCUMENTS

EP       0 243 031 A1   10/1987
JP       2004-358361 A  12/2004
(Continued)

OTHER PUBLICATIONS

The Extended European Search Report issued on Jun. 23, 2016 in European Patent Application No. 13859784.4.
(Continued)

*Primary Examiner* — Chee-Chong Lee
(74) *Attorney, Agent, or Firm* — Foley & Lardner LLP (57) ABSTRACT

A chamber (1) and an air conduit (7) connecting a liquid surface retaining hole (5) with an air hole (6) for supplying air from the outside of an electrostatic atomizer (50) to the chamber (1) are provided. When the liquid surface retaining hole (5) is blocked, the liquid supply from a liquid supplying section (3) to the chamber (1) will be stopped. The air conduit (7) has bent sections (8), and a space (10) for holding the liquid is formed in the air conduit (7).

3 Claims, 8 Drawing Sheets

(51) Int. Cl.
*B05B 5/03* (2006.01)
*B05B 5/057* (2006.01)
*B05B 5/16* (2006.01)
*B05B 5/025* (2006.01)

(52) U.S. Cl.
CPC ................ B05B 5/057 (2013.01); B05B 5/16 (2013.01); *A61M 2205/21* (2013.01)

(58) Field of Classification Search
USPC ........................................................ 239/704
See application file for complete search history.

(56) References Cited

U.S. PATENT DOCUMENTS

| | | | | |
|---|---|---|---|---|
| 3,729,142 | A * | 4/1973 | Rangel-Garza | A01G 25/023 138/42 |
| 5,971,215 | A * | 10/1999 | Bartsch | B05B 11/3059 222/153.13 |
| 6,328,543 | B1 * | 12/2001 | Benecke | A47L 13/20 222/383.1 |
| 6,626,332 | B2 * | 9/2003 | Ehrensperger | A47K 5/14 222/1 |
| 2004/0251326 | A1 | 12/2004 | Pirrie | |
| 2008/0277415 | A1 * | 11/2008 | Pirrie | B05B 5/1691 222/88 |
| 2010/0327089 | A1 | 12/2010 | Nakada et al. | |

FOREIGN PATENT DOCUMENTS

| | | | |
|---|---|---|---|
| JP | 2005-238034 | A | 9/2005 |
| JP | 2006-181544 | A | 7/2006 |
| JP | 2007-144293 | A | 6/2007 |
| JP | 2007-260674 | A | 10/2007 |
| JP | 2012-196777 | A | 10/2012 |
| WO | WO 2006/070739 | A1 | 7/2006 |
| WO | WO-2006/077389 | A2 | 7/2006 |
| WO | WO 2009/044939 | A1 | 4/2009 |
| WO | WO 2009/107513 | A1 | 9/2009 |

OTHER PUBLICATIONS

International Search Report corresponding to Application No. PCT/JP2013/082654, dated Mar. 11, 2014.
Translation of the International Preliminary Report on Patentability corresponding to Application No. PCT/JP2013/082654, Jun. 18, 2015.
Office Action issued in Chinese Patent Application No. 201380063750.7 mailed Nov. 3, 2016.

* cited by examiner

ELECTROSTATIC ATOMIZER

TECHNICAL FIELD

The present invention relates to an electrostatic atomizer that hardly causes leakage of a liquid to be sprayed.

BACKGROUND ART

Figure 6:
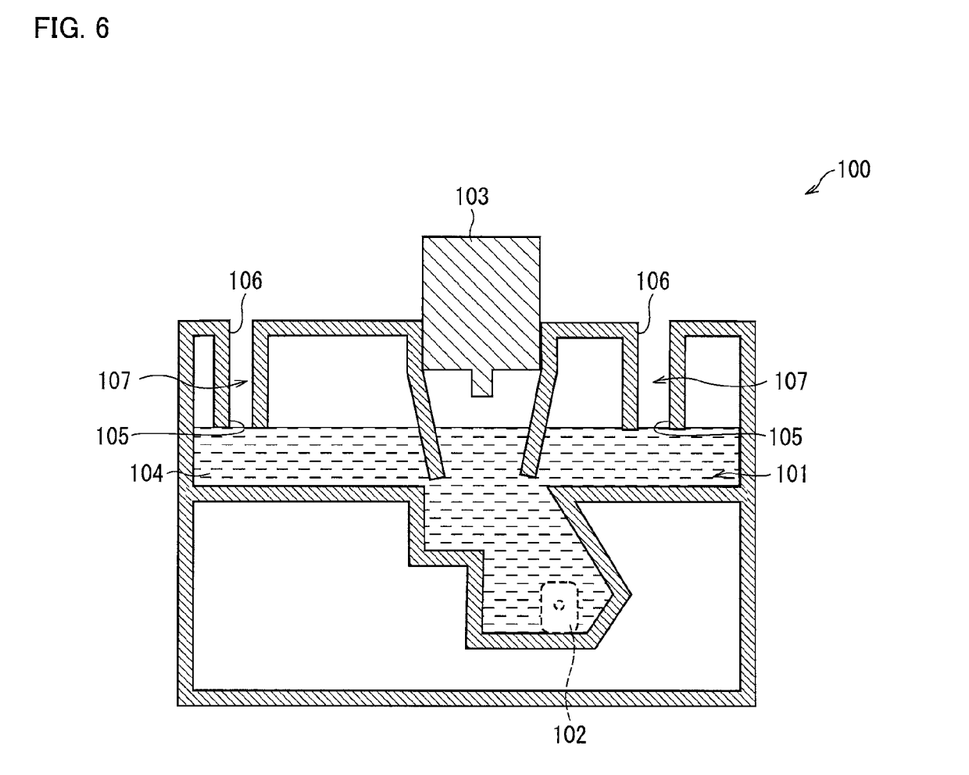
FIG. 6 is a cross-sectional view illustrating an electrostatic atomizer of a conventional technique.

Conventionally, an atomizer for spraying a liquid in a container via a spraying section has been widely used in various fields. A known example of such an atomizer is an electrostatic atomizer which atomizes and sprays a liquid by Electro Hydrodynamics (EHD). The electrostatic atomizer forms an electric field near a tip of the spraying section and uses the electric field to atomize and spray the liquid at the tip of the spraying section. FIG. 6 illustrates such an electrostatic atomizer.

An electrostatic atomizer 100 illustrated in FIG. 6 includes a chamber 101, a spraying section 102, and a liquid supplying section 103. A liquid 104 which has been supplied from the liquid supplying section 103 to the chamber 101 is sprayed from the spraying section 102. When the chamber 101 has been filled with the liquid 104, a liquid surface retaining hole 105 is blocked, and accordingly a flow of air from an air hole 106 to the chamber 101 is blocked. From this, supplying of the liquid 104 from the liquid supplying section 103 to the chamber 101 is stopped, and a liquid surface is retained at a constant level. As such, the liquid 104 is stored in the chamber 101, and the liquid 104 is sprayed from the spraying section 102 by utilizing an electric field.

SUMMARY OF INVENTION

Technical Problem

Under the circumstance that greater importance is being given to reduction in size, the conventional electrostatic atomizer 100 is demanded to have a simpler structure. In view of this, in the electrostatic atomizer 100, the liquid surface retaining hole 105 and the air hole 106 are connected with each other via a straight linear air conduit 107. With the configuration, in a case where the electrostatic atomizer 100 is tilted at a prescribed angle due to falling down, etc. of the electrostatic atomizer 100, the liquid 104 may flow from the liquid surface retaining hole 105 to the air hole 106, and accordingly the liquid 104 may leak the outside the electrostatic atomizer 100.

In view of the problem, an object of the present invention is to provide an electrostatic atomizer that hardly causes leakage of a liquid in a case where the electrostatic atomizer is tilted due to falling down, etc.

Solution to Problem

In order to attain the object, the electrostatic atomizer of the present invention is an electrostatic atomizer for spraying a liquid and includes: a chamber for storing the liquid supplied from a liquid supplying section; and an air conduit connecting a liquid surface retaining hole with an air hole, the air conduit being provided in the chamber, the liquid surface retaining hole being blocked or opened by the liquid depending on a level of a liquid surface of the liquid, and the air hole being provided so that air may be supplied from the outside of the electrostatic atomizer to the chamber via the air hole, wherein the atomizer is so designed that liquid supply from the liquid supplying section to the chamber will be stopped when the liquid surface retaining hole is blocked by the liquid, the air conduit has bent sections, and a space for holding the liquid is formed in the air conduit.

The air conduit has the bent section. From this, even in a case where the electrostatic atomizer is tilted due to falling down, etc. and the liquid flows in the air conduit via the liquid surface retaining hole, the liquid remains at the bent section, and therefore the liquid will not immediately leak from the air hole. Moreover, while the liquid remains, an amount of the liquid that flows to the liquid surface retaining hole increases, and consequently the liquid surface retaining hole is blocked by the liquid. This can stop the supply of the liquid from the liquid supplying section.

Further, in a case where the electrostatic atomizer is tilted due to falling down or the like, the liquid which has passed through the liquid surface retaining hole remains in the space, and it takes a long time for the liquid to reach the air hole. Consequently, it becomes difficult for the liquid to reach the air hole, and thus the electrostatic atomizer of the present invention brings about the effect of preventing leakage of the liquid.

Advantageous Effects of Invention

The electrostatic atomizer of the present invention includes: a chamber for storing the liquid supplied from a liquid supplying section; and an air conduit connecting a liquid surface retaining hole with an air hole, the air conduit being provided in the chamber, the liquid surface retaining hole being blocked or opened by the liquid depending on a level of a liquid surface of the liquid, and the air hole being provided so that air may be supplied from the outside of the electrostatic atomizer to the chamber via the air hole, wherein the atomizer is so designed that liquid supply from the liquid supplying section to the chamber will be stopped when the liquid surface retaining hole is blocked by the liquid, the air conduit has bent sections, and a space for holding the liquid is formed in the air conduit.

This makes it possible to bring about an effect of providing the electrostatic atomizer that hardly causes leakage of a liquid.

DESCRIPTION OF EMBODIMENTS

The following description will discuss an embodiment of the present invention with reference to FIGS. 1 through 5 and FIGS. 7 and 8. Note, however, that the present invention is not limited to this. In the following description, the same members and the same components are given the same reference signs, and have the same names and the same functions, and accordingly detailed descriptions thereof will not be repeated.

Note that a concept of "up-and-down" corresponds to up-and-down in a vertical direction. Each of a lateral direction and a horizontal direction indicates a direction perpendicular to the up-and-down direction.

Figure 1:
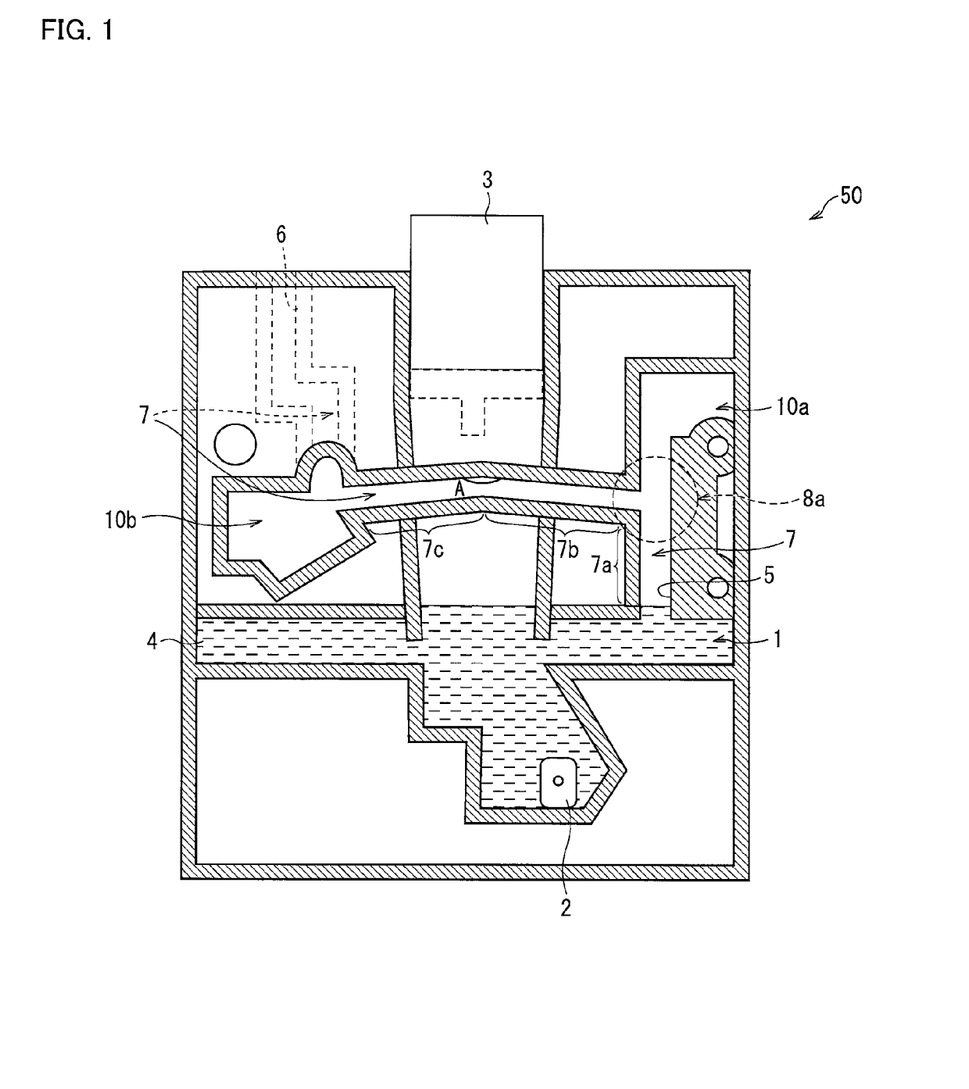
FIG. 1 is a cross-sectional view illustrating an electrostatic atomizer of the present invention.

FIG. 1 is a cross-sectional view illustrating an electrostatic atomizer 50 of the present invention viewed from a cross section including an air conduit 7, which is located in a center of the cross section, toward a liquid supplying section 3. That is, FIG. 1 is a cross-sectional view of the electrostatic atomizer 50 of the present invention, and the cross-sectional view of FIG. 1 includes cross sections of respective air conduits 7b and 7c which extend in the horizontal direction.

The electrostatic atomizer 50 includes a chamber 1 and a spraying section 2.

Figure 7:
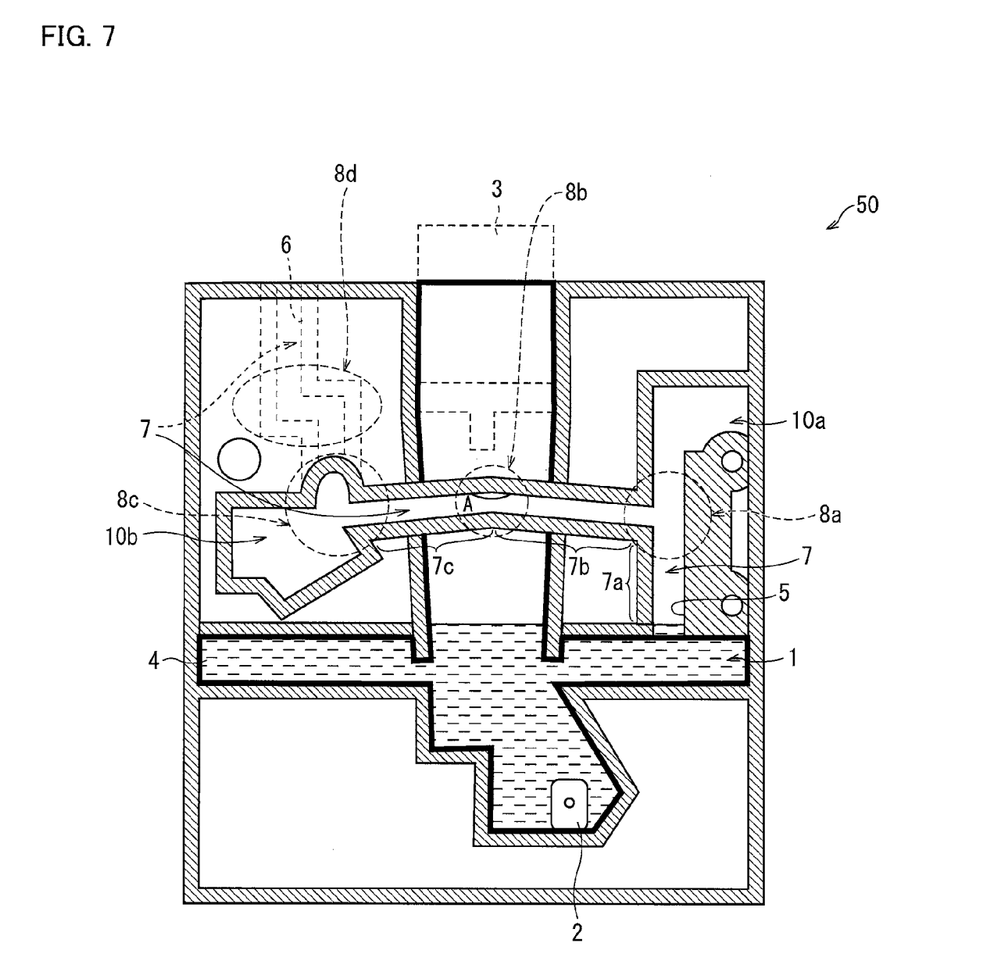
FIG. 7 is a view illustrating a chamber of the present invention.
Figure 8:
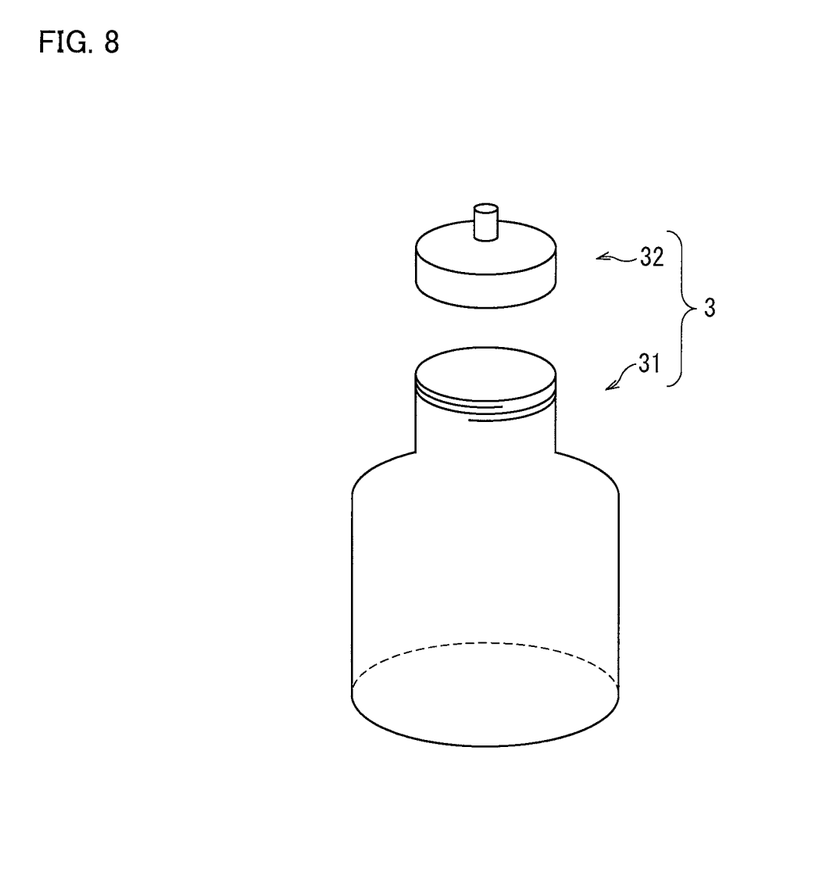
FIG. 8 is a perspective view illustrating an example of a liquid supplying section of the present invention.

The chamber 1 is a container having a space for storing the liquid 4. A capacity of the chamber 1 is determined based on conditions such as a size of the spraying section 2 or an amount of the liquid 4 to be consumed (i.e., sprayed). The capacity of the chamber 1 can be, for example, 200 mm$^3$. FIG. 7 is a view illustrating the chamber 1, and the liquid 4 is stored in the chamber 1 that is indicated by bold lines in FIG. 7.

In FIG. 7, the liquid supplying section 3 is indicated by dashed lines for easiness of viewing. The liquid supplying section 3 is a removable component that is attached to an upper part of the chamber 1. From the liquid supplying section 3, a liquid is supplied to the chamber 1 with a method which will be described later.

The spraying section 2 is a member used to spray aromatic oil, a chemical substance for an agricultural product, a medicine, an agricultural chemical, a pesticide, an air cleaning agent, and the like. The spraying section 2 sprays the liquid 4 to the outside of the electrostatic atomizer 50.

The liquid 4 is not limited to a particular one, provided that the liquid can be sprayed in a form of mist from the electrostatic atomizer 50 via the spraying section 2. Specifically, the liquid 4 can be a liquid that contains water and any of various components for pesticide, sterilization, fragrance, and the like. Examples of the components encompass the following known components, i.e., a synthetic pyrethroid compound; an organic phosphorous compound; a carbamate compound; a nereistoxin compound; a neonicotinoid compound; a benzoylurea compound; a phenylpyrazole compound; a hydrazine compound; an organochlorine compound; a natural pesticide; and other pesticides, repellents, synergists, and the like.

Moreover, a concentration of the component is not limited to a particular one and can be, for example, 0.05 mass % to 10 mass % relative to a total mass of the liquid. The concentration of the component can be adjusted by the use of a solvent such as water, dipropylene glycol monoethyl ether, ethanol, 1-propanol, 2-propanol, or 1-methoxy-2-propanol. Note that the liquid can contain a preservative, a surfactant, or the like, as appropriate.

Figure 2:
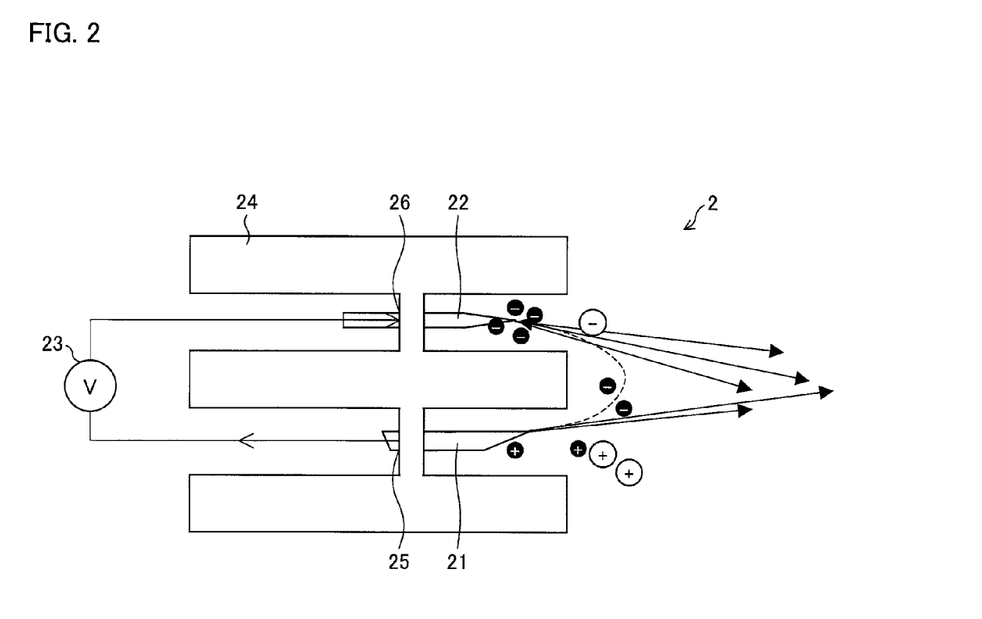
FIG. 2 is a plan view illustrating a spraying section included in the electrostatic atomizer of the present invention.

FIG. 2 is a plan view illustrating the spraying section 2. As illustrated in FIG. 2, the spraying section 2 at least includes a spray electrode 21, a reference electrode 22, a power supply device 23, and a dielectric 24. Alternatively, the spraying section 2 may be configured such that the power supply device 23 is provided outside of the spraying section 2 and the spraying section 2 is connected with the power supply device 23.

The spray electrode 21 includes a conductive conduit such as a metallic capillary (e.g., type 304 stainless steel) and a spray part which is a tip of the spray electrode 21. The spray electrode 21 is connected with the reference electrode 22 via the power supply device 23 and sprays a liquid from the spray part.

The reference electrode 22 is made of a conductive rod such as a metal pin (e.g., type 304 stainless steel). The spray electrode 21 and the reference electrode 22 are provided in parallel with each other with a prescribed distance therebetween.

The power supply device 23 applies a high voltage across the spray electrode 21 and the reference electrode 22. For example, the power supply device 23 applies a high voltage of 1 kV to 30 kV (e.g., 3 kV to 7 kV) across the spray electrode 21 and the reference electrode 22. The application of a high voltage forms an electric field between the electrodes. This causes an electric dipole inside the dielectric 24. In this case, the spray electrode 21 is positively charged, and the reference electrode 22 is negatively charged (alternatively, the spray electrode 21 may be negatively charged, and the reference electrode 22 may be positively charged). Then, a negative dipole occurs on a surface of the dielectric 24 which surface is closest to the positively-charged spray electrode 21, a positive dipole occurs on a surface of the dielectric 24 which surface is closest to the negatively-charged reference electrode 22, so that a charged gas and a charged substance species (i.e., liquid 4) are released as mist by the spray electrode 21 and the reference electrode 22.

The dielectric 24 is not limited in particular, provided that the dielectric 24 is made of a resin. Examples of the resin encompass resins such as polypropylene, nylon 6, nylon 11, nylon 12, nylon 66, and a polyacetyl-polytetrafluoroethylene mixture. The dielectric 24 supports the spray electrode 21 at a spray electrode fixing part 25 and supports the reference electrode 22 at a reference electrode fixing part 26.

The following further describes the electrostatic atomizer 50 with reference to FIG. 1.

The liquid supplying section 3 is removably attached to an upper part of the electrostatic atomizer 50. Specifically, the liquid supplying section 3 is removably attached to an upper part of the chamber 1. A liquid is stored in the liquid supplying section 3, and the liquid 4 stored in the liquid supplying section 3 is supplied to the chamber 1.

FIG. 8 is a perspective view illustrating an example of the liquid supplying section 3.

As illustrated in FIG. 8, the liquid supplying section 3 includes a container body 31 and a cap 32. In the container body 31, a liquid is stored. A material of the container body 31 is not limited to a particular one and can be plastic, glass, or the like. A size and a shape of the container body 31 are not limited to particular ones, provided that the container body 31 can be attached to the chamber 1. The lid 32 is removably attached to an opening of the container body 31 with a known method such as fitting or twisting. The lid 32 has an opening so that a liquid may flow out through the opening. A material of the lid 32 is not limited to a particular one and can be plastic or the like. A size and a shape of the lid 32 are not limited to particular ones. The liquid supplying section 3 (more specifically, a structure of the lid 32) is not limited to a particular structure, provided that a liquid can be supplied to the chamber 1 with a method which will be described later.

Note that the liquid supplying section 3 can be regarded as a part of the electrostatic atomizer 50 or can be regarded as being separate from the electrostatic atomizer 50.

Next, a liquid surface retaining hole 5, an air hole 6, and an air conduit 7 are described with reference to FIG. 1.

The air hole 6 is provided in an outer surface of the electrostatic atomizer 50 and is connected with the air conduit 7. According to the electrostatic atomizer 50, air (ambient air) is supplied from the outside of the electrostatic atomizer 50 to the chamber 1 via the air hole 6, the air conduit 7, and the liquid surface retaining hole 5. From this, a location at which the air hole 6 is provided is not limited to a particular one, provided that the air hole 6 is provided in the outer surface of the electrostatic atomizer 50. That is, the air hole 6 can be provided in an upper surface or a lateral surface of the electrostatic atomizer 50. The air hole 6 is preferably provided in the upper surface of the electrostatic atomizer 50. This makes it possible to inhibit leakage of the liquid 4 from the chamber 1 provided in the electrostatic atomizer 50.

It is preferable that the number of locations at which the air hole 6 is provided is as small as possible because the leakage of a liquid from the chamber 1 to the outside of the electrostatic atomizer 50 further hardly occurs. In view of this, the air hole 6 is preferably provided at one location of the electrostatic atomizer 50. Note, however, that the number of locations at which the air hole 6 is provided is not limited to one, and can be a plural number.

The liquid surface retaining hole 5 is provided in the chamber 1, and the liquid surface retaining hole 5 and the air hole 6 are connected to each other via the air conduit 7. The liquid surface retaining hole 5 is provided so that ambient air can enter the chamber 1 via the liquid surface retaining hole 5. The liquid surface retaining hole 5 is blocked or opened by the liquid 4 in the chamber 1 depending on a liquid surface level of the liquid 4. That is, in a case where the liquid surface level is identical with or higher than a height at which the liquid surface retaining hole 5 is provided, the liquid surface retaining hole 5 is blocked by the liquid 4. In a case where the liquid surface level is lower than the height at which the liquid surface retaining hole 5 is provided, the liquid surface retaining hole 5 is free from the liquid 4, so that the chamber 1 is opened to the atmosphere.

A diameter (or a length of a longest side in a case of a polygonal shape) of the liquid surface retaining hole 5 and the air hole 6 is not limited to a particular one and can be, for example, a diameter of 0.5 mm or more and 3 mm or less. A shape of the liquid surface retaining hole 5 and the air hole 6 is not limited to a particular one and can be, for example, a circular shape; an elliptical shape; and polygonal shapes such as a triangular shape, quadrangular shapes such as a rectangular shape and a square shape, a pentagonal shape, and a hexagonal shape. In view of preventing leakage of liquid from the air hole 6, a linear distance between the liquid surface retaining hole 5 and the air hole 6 is preferably long.

The air conduit 7 is a conduit connected to the liquid surface retaining hole 5 and the air hole 6, and is an air passage for allowing the chamber 1 to be opened to the atmosphere. In a case where the liquid surface retaining hole 5 is not blocked by the liquid 4, the chamber 1 is opened to the atmosphere via the liquid surface retaining hole 5, the air hole 6, and the air conduit 7.

More specifically, as shown in FIG. 1, the air conduit 7 includes at least (i) an air conduit 7a (first portion) which extends in a direction (first direction) perpendicular to a liquid surface of a liquid stored in the chamber 1, (ii) an air conduit 7b (second portion) which extends in a second direction (i.e., a direction of an axis 9 in FIG. 4) that forms, with the liquid surface, an angle smaller than an angle between the first direction and the liquid surface, and (iii) an air conduit 7c (third portion) which is continuous with the air conduit 7b and is located closer to the air hole 6 than the air conduit 7b is.

A bent section (first bent section) 8a, which is one of bent sections 8, is provided between the air conduit 7a and the air conduit 7b. The air conduit 7b is inclined with respect to the liquid surface such that the bent section 8a side thereof may come closer to the liquid surface. Moreover, the air conduit 7c is inclined with respect to the liquid surface such that a side opposite to the bent section 8a may come closer to the liquid surface.

Further, on the bent section 8a side of the air conduit 7b, a liquid retaining space (first space) 10a which is connected with the air conduit 7a and the air conduit 7b is provided for storing a liquid. Moreover, on a side of the air conduit 7c which side is opposite to the bent section 8a, a liquid retaining space (second space) 10b is provided which is connected with the air conduit 7c.

In FIG. 1, the air conduit 7a extends in the direction perpendicular to the liquid surface (first direction). Note, however, that the air conduit 7a can extend in a direction inclined with respect to the liquid surface.

The term "liquid surface" indicates a surface of a liquid in an expected installation state of the electrostatic atomizer 50 in use. The electrostatic atomizer 50 is expected to be installed such that a bottom surface of the electrostatic atomizer 50 may become horizontal.

Details of the bent sections 8 and the liquid retaining space 10 will be described later. Note that the liquid retaining spaces 10a and 10b are collectively referred to simply as "liquid retaining space 10" when the liquid retaining spaces 10a and 10b do not need to be distinguished.

A diameter of the air conduit 7 is not limited to a particular one and can be, for example, 0.5 mm or more and 3 mm or less. Moreover, a shape of the air conduit 7 is not limited to a particular shape and can be, for example, a circular shape; an elliptical shape; and polygonal shapes such as a triangular shape, quadrangular shapes such as a rectangular shape and a square shape, a pentagonal shape, and a hexagonal shape.

A length of the air conduit 7, that is, a distance between the liquid surface retaining hole 5 and the air hole 6 varies depending on an amount of the liquid 4 stored in the chamber 1, and can be, for example, 11 mm or more and 100 mm or less.

Next, the following describes how a liquid is supplied from the liquid supplying section 3 to the chamber 1.

According to the electrostatic atomizer 50, a liquid flows from the liquid supplying section 3 to the chamber 1 in a case where a pressure in the chamber 1 is the atmospheric pressure (i.e., 1 atm), in other words, in a case where the chamber 1 is opened to the atmosphere via the liquid surface retaining hole 5, the air hole 6, and the air conduit 7. Meanwhile, in a case where the liquid surface retaining hole 5 has been blocked by the liquid and accordingly the chamber 1 is isolated from the outside of the electrostatic atomizer 50, the liquid may continue to flow from the liquid supplying section 3 to the chamber 1 for a while, but eventually the flow of the liquid stops. In this state, the liquid 4 is not supplied from the liquid supplying section 3, and therefore the liquid surface of the liquid 4 is held.

As such, the supply and the stop of the liquid 4 to the chamber 1 are switched depending on an internal pressure of the chamber 1. Therefore, the electrostatic atomizer 50 is favorably used because it is unnecessary to carry out complicated control.

Subsequently, in a case where the liquid 4 is sprayed from the spraying section 2 and the liquid surface in the chamber 1 descends due to consumption (atomization) of the liquid 4, the liquid surface retaining hole 5 becomes free from the liquid 4, and accordingly the chamber 1 is opened to the atmosphere. Then, the liquid 4 is supplied from the liquid supplying section 3 to the chamber 1 again, and the liquid surface ascends and is held at a prescribed level.

Figure 3:
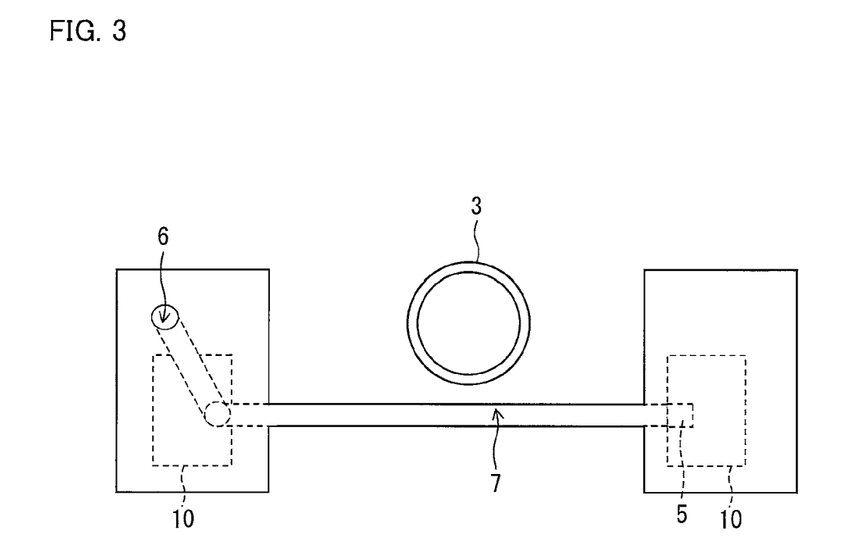
FIG. 3 is a plan view schematically illustrating an air conduit in the electrostatic atomizer of the present invention.

FIG. 3 is a plan view schematically illustrating a path of the air conduit 7. The air conduit 7 is provided from the liquid surface retaining hole 5 to the air hole 6 so as to pass through the vicinity of the liquid supplying section 3. As a preferable configuration, the air hole 6 is located on a farther side (i.e., an upper side in FIG. 3) than a part of the air conduit 7, which part extends in the lateral direction at a location that is in front of the liquid supplying section 3 (i.e., than a part of the air conduit 7 which part is depicted by solid lines in FIG. 3). In other words, the air hole 6 is not located on an extension of the part of the air conduit 7 which part is depicted by solid lines, when viewed from above as in the plan view of FIG. 3. This means that the air conduit 7 has a bent portion (bent section) in the path to the air hole 6. With the configuration, even in a case where a liquid enters the part of the air conduit 7 which part extends in the lateral direction, the liquid will not immediately leak from the air hole 6.

Moreover, in a condition in which the electrostatic atomizer 50 is standing and a direction in which gravitational force is applied is assumed to be downward, the liquid supplying section 3 is preferably located upper than the chamber 1 and the air conduit 7 preferably has inclinations so as to be convexed upward. The "state where the electrostatic atomizer 50 is standing" means a state in which the liquid supplying section 3 is located on an upper side than the chamber 1 and the electrostatic atomizer 50 is not falling down. The "inclinations so as to be convexed upward" means that the air conduit 7 has an inclination from one lower side to an upper side and an inclination from a highest part of the upper side to the other lower side.

In other words, in a case where the air conduit 7 has a part that extends in the horizontal direction in the cross-sectional view of FIG. 1, the part has a convex portion protruding upward. In FIG. 1, the convex portion protruding upward is provided in the air conduit 7 so that an angle A in FIG. 1 may become smaller than 180 degrees. From this, even in a case where a liquid enters the convex portion (i.e., the inclinations convexed upward) of the air conduit 7, the liquid flows rightward or leftward in FIG. 1, and the liquid will not remain in the air conduit 7. It is therefore possible to prevent a case in which the air conduit 7 is clogged with the liquid.

Alternatively, the air conduit 7 can have an inclined portion that is inclined with respect to the horizontal direction, instead of the convex portion protruding upward. With this configuration also, the liquid will not remain in the air conduit 7, and it is therefore possible to prevent a case in which the air conduit 7 is clogged with the liquid.

Next, the following describes the bent section 8.

Figure 4:
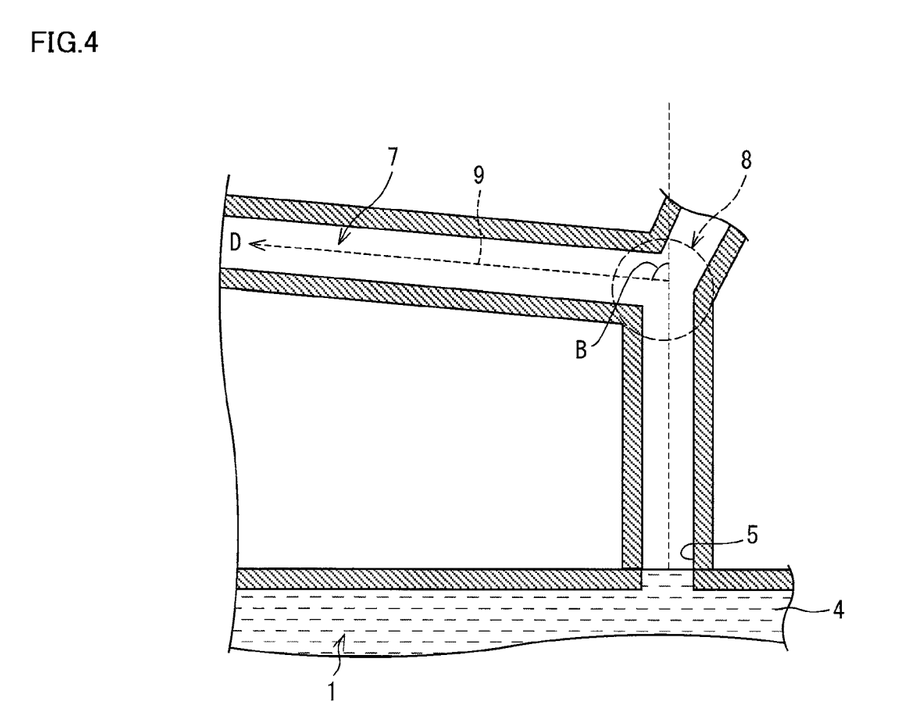
FIG. 4 is a cross-sectional view illustrating a bent section in the electrostatic atomizer of the present invention.
Figure 5:
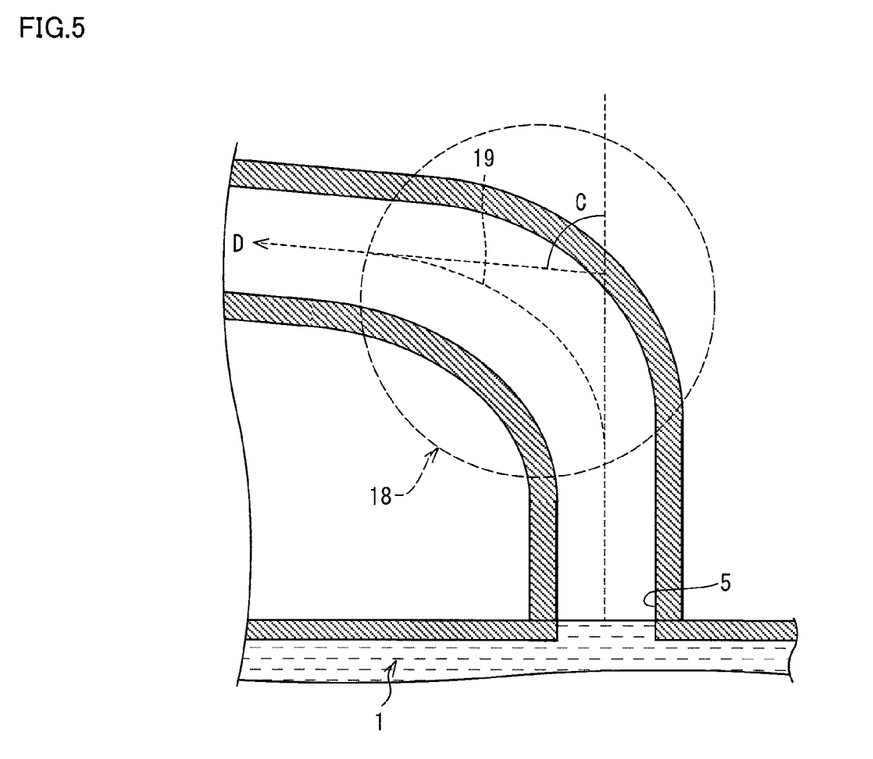
FIG. 5 is a cross-sectional view illustrating a modification example of the bent section in the electrostatic atomizer of the present invention.

In the electrostatic atomizer 50, the air conduit 7 has the bent section 8 in order to prevent leakage of a liquid. The bent section 8 is a space or a portion at which the air conduit 7 is bent. The air conduit 7 is bent. Since the bent section 8 is provided, even in a case where the electrostatic atomizer 50 is tilted due to falling down, etc. and the liquid 4 flows in the air conduit 7 via the liquid surface retaining hole 5, the liquid 4 remains at the bent section 8, and therefore the liquid will not immediately leak from the air hole 6. Moreover, while the liquid 4 remains, an amount of the liquid 4 that flows to the liquid surface retaining hole 5 increases, and consequently the liquid surface retaining hole 5 is blocked by the liquid 4. This can stop the supply of the liquid 4 from the liquid supplying section 3. As such, the electrostatic atomizer 50 brings about an effect of preventing liquid leakage and can control the liquid surface level.

In most cases, the electrostatic atomizer of this type is small in size, and a structure thereof is usually simplified. According to the electrostatic atomizer 100 illustrated in FIG. 6, simplification of the device is prioritized, and therefore the air conduit 107 has a straight line shape. From this, the leakage of a liquid is prevented mainly by placing the device in a stable state. On the other hand, the present invention is accomplished based on a finding which has been made by carefully checking again the simple structure of the electrostatic atomizer, i.e., the finding that the leakage of a liquid is prevented by providing the bent section in the air conduit.

The following description will discuss the bent section 8 in detail with reference to FIG. 4. FIG. 4 is a cross-sectional view of the bent section 8 in the electrostatic atomizer 50.

As illustrated in FIG. 4, the bent section 8 that constitutes one of inclinations of the convexed air conduit 7 is bent at 85° with respect to the vertical direction. That is, the axis 9 is bent with respect to the vertical direction by an angle B in FIG. 4. A bent section that constitutes the other of inclinations of the convexed air conduit 7 is also bent at 85° with respect to the vertical direction. From this, the inclinations of the convexed air conduit 7 are 5° on the one side (i.e., a right-hand side in FIG. 4) and 5° on the other side (i.e., a left-hand side in FIG. 4).

In other words, in the electrostatic atomizer 50, the air conduit 7 which extends in the vertical direction (i.e., the up-and-down direction in the drawing, the first direction) is bent in a direction of the axis 9 (i.e., the second direction), that is, the air conduit 7 is bent with respect to the vertical direction by the angle B. A part at which the air conduit 7 is bent is the bent section 8. The angle B in FIG. 4 is 85°. The bent section that constitutes the other of the inclinations of the convexed air conduit 7 is similarly bent at 85°. Therefore, the inclinations of the convexed air conduit 7 are respectively 5° on the one side (i.e., right side in the drawing) and 5° on the other side (i.e., left side in the drawing) with respect to the horizontal direction.

Even if the liquid 4 enters the air conduit 7, the liquid 4 tends to flow along the inclinations forming the upward convex, and it is therefore possible to provide the electrostatic atomizer in which the air conduit 7 is hardly blocked. The angle B of the bent section is not limited to a particular one and can fall within a range of larger than 0° and smaller than 90°. As the angle B is closer to 90°, a size of the electrostatic atomizer 50 can be reduced. Note that the inclinations of the convexed air conduit 7 on respective right and left sides of a highest part of the convex can have different angles with respect to the horizontal direction.

Alternatively, a bent section 18 can be smoothly curved as illustrated in FIG. 5. In the bent section 18, an axis 19 is smoothly curved along a direction in which the air conduit 7 is bent with respect to the vertical direction, and an angle C of the bent section 18 illustrated in FIG. 5 is 85°. As such, the air conduit 7 is bent at 85° with respect to the vertical direction. Note that the angle C is an angle formed between the vertical direction and an axis in a direction (i.e., direction D in FIG. 5) that extends straight along the air conduit 7 which has been smoothly curved at the bent section 18. In view of appropriately preventing leakage of a liquid, the angle C at the bent section 18 is not limited to a particular one and can fall within a range of larger than 0° and smaller than 90°.

Note that the bent section 8 is a space or a part at which the air conduit 7 is bent. Therefore, parts indicated by reference signs 8b, 8c, and 8d in FIG. 7 are also included in the bent section 8.

Moreover, as a preferable configuration, the air conduit 7 of the present invention has the liquid retaining space 10 for holding a liquid in the air conduit 7, as illustrated in FIG. 1.

In a case where the electrostatic atomizer 50 including the liquid retaining space 10 is tilted due to falling down or the like, the liquid 4 which has passed through the liquid surface retaining hole 5 remains in the liquid retaining space 10, and it takes a long time for the liquid 4 to reach the air hole 6. Consequently, it becomes difficult for the liquid 4 to reach the air hole 6, and it is therefore possible to prevent leakage of the liquid from the air hole 6.

The number of the liquid retaining space 10 is not limited to one, and can be two as in the electrostatic atomizer 50 or can be three or more. In a case where the number of the liquid retaining spaces 10 is two or more, the liquid retaining spaces 10 are preferably provided in different directions, different locations, and the like, as in the electrostatic atomizer 50. From this, it is possible to cause a large amount of the liquid 4 to remain in any of the liquid retaining spaces 10. For example, in a case where one of the liquid retaining spaces 10 has an angle at which the liquid 4 enters less and the other of the liquid retaining spaces 10 has a different angle at which the liquid 4 enters, it is possible to cause a large amount of the liquid 4 to remain in the other of the liquid retaining spaces 10.

A capacity of the liquid retaining space 10 is set based on an amount of the liquid 4 that can be stored in the chamber 1 and an amount of the liquid 4 that is to be supplied from the liquid supplying section 3 to the chamber 1. For example, the capacity of the liquid retaining space 10 can be 100 mm$^3$ or more and 200 mm$^3$ or less. By thus providing the liquid retaining space 10 in the air conduit 7 while effectively utilizing an inner space of the electrostatic atomizer in response to the demand of reducing the size of the electrostatic atomizer, it is possible to effectively prevent leakage of the liquid from the electrostatic atomizer 50.

Further, the electrostatic atomizer 50 preferably includes a porous body in the liquid retaining space 10. The porous body can be a member in which a plurality of fine pores are provided and a member which makes the flow of the liquid 4 slow by bringing itself contact with the liquid 4 that is flowing through the air conduit 7. Note, however, that the porous body does not block the air conduit 7. Examples of the porous body encompass an open-cell resin body made of polyurethane, polyethylene, polyethylene terephthalate, polyvinyl formal, polystyrene, or the like; a porous body obtained by tableting and sintering, as a main component, resin fine particles of polyethylene, polypropylene, nylon, or the like; a porous body made of polyethylene fluoride or the like; a felt member made of polyester, polypropylene, nylon, acrylic resin, rayon, wool, or the like; a resin fiber assembly such as nonwoven fabric made up of polyolefin fibers, polyester fibers, nylon fibers, rayon fibers, acrylic fibers, vinylon fibers, polychlal fibers, aramid fibers, or the like; and a porous sintered body of inorganic powder, which porous sintered body has been obtained by tableting and sintering inorganic powder of ceramic or the like as a main component. Note, however, that the porous body is not limited to these.

By thus providing the porous body in the liquid retaining space 10, a flow velocity of the liquid 4 which has entered the liquid retaining space 10 decreases, and therefore the liquid 4 very easily remains in the liquid retaining space 10. From this, it becomes difficult for the liquid 4 to reach the air hole 6, and this makes it possible to further easily prevent leakage of liquid. This is a highly preferable configuration of the electrostatic atomizer of the present invention.

EXAMPLE

Example 1

The electrostatic atomizer 50 illustrated in FIG. 1 was caused to fall down successively in four directions, i.e., frontward, backward, rightward, and leftward, and then presence or absence of leakage of a liquid was checked. After that, the electrostatic atomizer 50 was restored to a former state, and then presence or absence of leakage of a liquid was checked. Note that, in the electrostatic atomizer 50, (i) two liquid retaining spaces 10 each having a capacity of 200 mm$^3$ were provided, (ii) the angle A of the air conduit 7 was 170°, and (iii) each of right and left parts of the air conduit 7 was inclined by 5°.

The electrostatic atomizer 50 was set to the following conditions:

Capacity of chamber 1: 200 mm$^3$

Diameter of liquid surface retaining hole 5 (quadrangular shape): 1 mm

Diameter of air hole 6 (circular shape): 1 mm

Length of air conduit 7 (length of axis): 26 mm

Linear distance between liquid surface retaining hole 5 and air hole 6: 11 mm The liquid supplying section 3 was filled with 25 g of a formulation as the liquid 4, and was then sealed. A ratio of components in the formulation was as follows: 88% of dipropylene glycol monoethyl ether, 5% of isoparaffin, 5% of polyethylene glycol, and 2% of 0.4% sodium acetate aqueous solution.

After the liquid supplying section 3 was sealed, the liquid supplying section 3 was attached to the electrostatic atomizer 50, and then a liquid was started to be supplied from the liquid supplying section 3 to the chamber 1. Next, it was confirmed that air no longer enters via the air hole 6, and it was thus determined that the liquid surface of the liquid 4 became constant in the chamber 1.

Subsequently, the electrostatic atomizer 50 was (1) caused to fall down at 90° frontward (i.e., to a viewer side of FIG. 1) and left the electrostatic atomizer 50 in that state for 30 minutes, and then whether or not the liquid 4 leaked from the air hole 6 was checked. As a result, no leakage of the liquid occurred. Next, the electrostatic atomizer 50 that was in the state illustrated in FIG. 1 was (2) caused to fall down at 90° backward (i.e., to a side opposite to the viewer side of FIG. 1) and left the electrostatic atomizer 50 in that state for 30 minutes, and then whether or not the liquid 4 leaked from the air hole 6 was checked. As a result, no leakage of the liquid occurred.

Next, the electrostatic atomizer 50, which had been confirmed, by the above operations (1) and (2), to cause no leakage of the liquid, was (3) caused to fall down at 90° rightward (i.e., to a right side in FIG. 1) and left the electrostatic atomizer 50 in that state for 30 minutes, and then whether or not the liquid 4 leaked from the air hole 6 was checked. As a result, no leakage of the liquid occurred. Further, the electrostatic atomizer 50 that was in the state illustrated in FIG. 1 was (4) caused to fall down at 90° leftward (i.e., to a left side in FIG. 1) and left the electrostatic atomizer 50 in that state for 30 minutes, and then whether or not the liquid 4 leaked from the air hole 6 was checked. As a result, no leakage of the liquid occurred.

Lastly, (5) the electrostatic atomizer 50 which was falling down leftward was restored to the standing state illustrated in FIG. 1 and left the electrostatic atomizer 50 in that state for 24 hours, and then whether or not the liquid 4 leaked from the air hole 6 was checked. As a result, no liquid leakage occurred. As such, the electrostatic atomizer 50 of the present invention causes no leakage of the liquid from the air hole 6, and usefully solves the problem of the conventional electrostatic atomizer.

The present invention is not limited to the embodiments, but can be altered by a skilled person in the art within the scope of the claims. That is, an embodiment derived from a proper combination of technical means appropriately modified within the scope of the claims is also encompassed in the technical scope of the present invention.

[Remarks]

In order to attain the object, the electrostatic atomizer of the present invention is an electrostatic atomizer for spraying a liquid and includes: a chamber for storing the liquid; and a liquid supplying section for supplying a liquid to the chamber in a case where the chamber is at atmospheric pressure, the chamber having a liquid surface retaining hole which is blocked or opened by the liquid depending on the liquid surface level of the liquid, the liquid surface retaining hole being connected with an air hole via an air conduit, the air hole being provided so that air can be supplied from the outside of the electrostatic atomizer to the chamber, the air conduit having a bent section, and a space for holding the liquid being formed in the air conduit.

The air conduit has the bent section. From this, even in a case where the electrostatic atomizer is tilted due to falling down and the liquid flows in the air conduit via the liquid surface retaining hole, the liquid remains at the bent section, and therefore the liquid will not immediately leak from the air hole. Moreover, while the liquid remains, an amount of the liquid that flows to the liquid surface retaining hole increases, and consequently the liquid surface retaining hole is blocked by the liquid. This can stop the supply of the liquid from the liquid supplying section.

Further, in a case where the electrostatic atomizer is tilted due to falling down or the like, the liquid which has passed through the liquid surface retaining hole remains in the space, and it takes a long time for the liquid to reach the air hole. Consequently, it becomes difficult for the liquid to reach the air hole, and thus the electrostatic atomizer of the present invention brings about the effect of preventing leakage of the liquid.

According to the electrostatic atomizer of the present invention, in a condition in which the electrostatic atomizer is standing and a direction in which gravitational force is applied is assumed to be downward, the liquid supplying section is preferably located upper than the chamber and the air conduit preferably has inclinations so as to be convexed upward.

With the shape of the air conduit, even if the liquid enters the air conduit, the liquid tends to flow along the inclinations and it is therefore possible to provide the electrostatic atomizer in which the air conduit is hardly blocked.

INDUSTRIAL APPLICABILITY

The present invention is suitably applicable to an electrostatic atomizer.

REFERENCE SIGNS LIST

1: Chamber
2: Spraying section
3: Liquid supplying section
4: Liquid
5: Liquid surface retaining hole
6: Air hole
7, 7a, 7b, 7c: Air conduit
8, 18, 8a, 8b, 8c, 8d: Bent section
10, 10a, 10b: Liquid retaining space
50: Electrostatic atomizer

The invention claimed is:

1. An electrostatic atomizer for spraying a liquid, said electrostatic atomizer comprising:
  a chamber for storing the liquid supplied from a liquid supplying section; and
  an air conduit connecting a liquid surface retaining hole with an air hole, the air conduit being provided in the chamber, the liquid surface retaining hole being blocked or opened by the liquid depending on a level of a liquid surface of the liquid, and the air hole being provided so that air may be supplied from the outside of said electrostatic atomizer to the chamber via the air hole,
  wherein said atomizer is so designed that liquid supply from the liquid supplying section to the chamber will be stopped when the liquid surface retaining hole is blocked by the liquid,
  the air conduit has bent sections, and
  a space for holding the liquid is formed in the air conduit, and
  wherein:
  the air conduit has inclinations so as to be convexed away from the liquid surface;
  the air conduit has a first portion that extends in a first direction which is perpendicular to or inclined with respect to the liquid surface and a second portion that extends in a second direction whose angle with respect to the liquid surface is smaller than that of the first direction;
  a first bent section is provided between the first portion and the second portion as one of the bent sections; and
  the second portion is inclined with respect to the liquid surface so that a first bent section side thereof may be located closer to the liquid surface.

2. The electrostatic atomizer as set forth in claim 1, wherein:
  the air conduit has a third portion which is continuous with the second portion, the third portion being closer to the air hole than the second portion is;
  the third portion is inclined with respect to the liquid surface so that an opposite side of the first bent section thereof is located closer to the liquid surface than the side of the first bent section thereof.

3. The electrostatic atomizer as set forth in claim 2, wherein:
  a first space is provided on a side of the second portion as one of spaces for holding the liquid, the side of the second portion being closer to the first bent section; and a second space is provided on a side of the third portion as another one of the spaces for holding the liquid, the side of the third portion being an opposite side of the first bent section.

* * * * *